United States Patent [19]

Redecker et al.

[11] 4,125,561
[45] Nov. 14, 1978

[54] PROCESS FOR PRODUCTION OF TEREPHTHALIC DIALDEHYDE

[75] Inventors: Klaus Redecker, Porz-Wahn-Heide; Hermann Richtzenhain, Much-Schwellenbach, both of Germany

[73] Assignee: Dynamit Nobel Aktiengesellschaft, Troisdorf, Germany

[21] Appl. No.: 777,800

[22] Filed: Mar. 15, 1977

Related U.S. Application Data

[63] Continuation of Ser. No. 350,857, Apr. 13, 1973, abandoned.

[30] Foreign Application Priority Data

Apr. 13, 1972 [DE] Fed. Rep. of Germany ....... 2217782

[51] Int. Cl.² ............................................. C07C 45/00
[52] U.S. Cl. .................................................. 260/599
[58] Field of Search ....................................... 260/599

[56] References Cited

U.S. PATENT DOCUMENTS

| | | | |
|---|---|---|---|
| 2,948,756 | 8/1970 | Bengelsdorf | 260/599 |
| 3,524,885 | 8/1970 | Deinet | 260/599 |

Primary Examiner—Bernard Helfin
Attorney, Agent, or Firm—Sprung, Felfe, Horn, Lynch & Kramer

[57] ABSTRACT

Process for the production of terephthalic dialdehyde by hydrolysis of $\alpha,\alpha,\alpha',\alpha'$-tetrachloro-p-xylene, which comprises contacting $\alpha,\alpha,\alpha',\alpha'$-tetrachloro-p-xylene and steam in a reaction zone at a temperature and for a time sufficient for hydrolysis of the $\alpha,\alpha,\alpha',\alpha'$-tetrachloro-p-xylene to form said dialdehyde.

16 Claims, 1 Drawing Figure

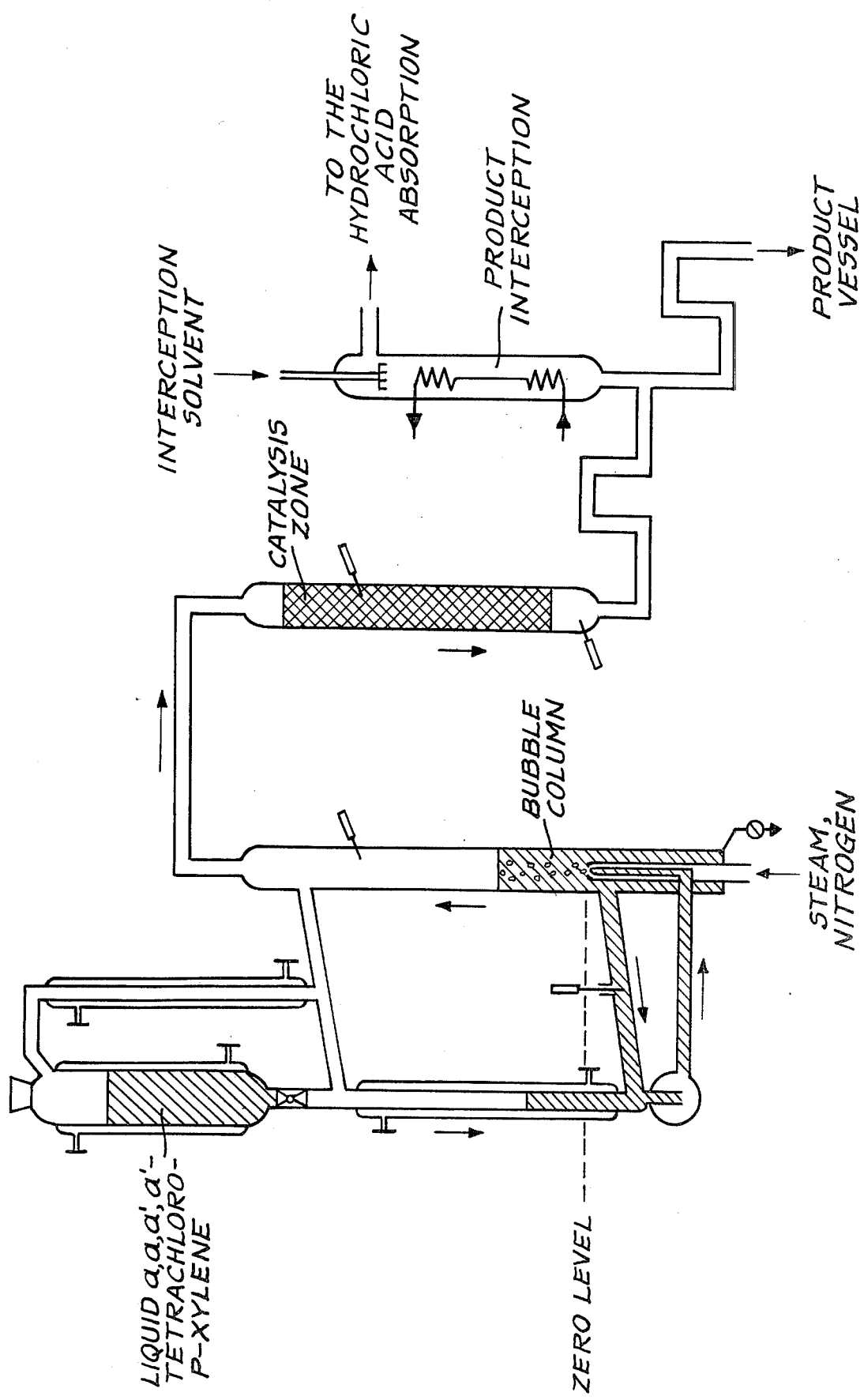

PROCESS FOR PRODUCTION OF TEREPHTHALIC DIALDEHYDE

This is a continuation, of application Ser. No. 350,857, filed Apr. 13, 1973 and now abandoned.

BACKGROUND

The present invention relates to a continuous process for the preparation of terephthalic aldehyde, i.e. the dialdehyde, through hydrolysis of $\alpha,\alpha,\alpha',\alpha'$-tetrachloro-p-xylene in the presence of catalysts.

Through the side-chain halogenation of p-xylene with radically excited chlorine or bromine, $\alpha,\alpha,\alpha',\alpha'$-tetrahalogen-p-xylene can be obtained, which is easily hydrolyzed at elevated temperature in the presence of catalysts by means of sulfuric acid according to the following sources: Belgian Pat. 667,022; M. Hoenig, Monatshefte 9, 1153; J. Thiele, O. Guenther, A. 347, 106–111 (1906); A. Weissberger, H. Bach, Ber. 65 (1932) 24, 28; Ruzicka, Buijs, Stoll, Helv. 15 (1932) 1220, 1222; Deluchat, A. (11) 1 (1934) 181, 207, 209; J. M. Snell, A. Weissberger, Org. Synth. Col., Vol. III (1955) 788, or by means of water according to A. Colson, H. Gautier, Bull. Soc. Chim. France (2) 45, 508 (1886); A. (6) 11, 28 (1887), G. Arditti, L. Palfray, C.r. 223., 548 (1946), and French Patent No. 2,059,339, either a great excess of water being used, from which the aldehyde can be obtained after the hydrolysis, or the hydrolysis being performed with the stoichiometric amount of water in the presence of preferably 0.5 to 30 m moles of iron salts per mole of dichloromethyl group, in a temperature range of 40° to 140° C., in accordance with French Pat. No. 2,059,339 (1970), the water being supplied in liquid form and the product being obtained in liquid form.

THE INVENTION

The present invention concerns a process for the continuous hydrolysis of $\alpha,\alpha,\alpha',\alpha'$-tetrachloro-p-xylene to terephthalic aldehyde with superheated steam optionally in the presence of catalysts, especially iron and zinc compounds, the dialdehyde that forms being removed as vapor.

It is known that terephthalic aldehyde is volatile with water vapor (Loew, A. 231, 364). This volatility is utilized in the present invention to remove from the reaction mixture the terephthalic aldehyde that has been formed by the hydrolysis of $\alpha,\alpha,\alpha',\alpha'$-tetrachloro-p-xylene in the presence of catalysts or without the presence thereof, the hydrolysis and the volatility of the $\alpha,\alpha,\alpha',\alpha'$-tetrachloro-p-xylene concurring with one another. It has furthermore been found that $\alpha,\alpha,\alpha',\alpha'$-tetrachloro-p-xylene and p-dichloromethyl-benzaldehyde are also volatile and sublimable, respectively. These or mixtures thereof with terephthalic aldehyde may be reacted completely with the water vapor in a succeeding catalysis zone. By cooling the vapor phase, terephthalic aldehyde may be precipitated in solid form, or it may be obtained from the vapor by extraction or interception with an inert solvent such as a chlorinated hydrocarbon with 1 to 6 carbon atoms or hydrocarbons such as benzene, or it may be isolated in some other way.

It is possible to make the hydrolysis take place almost completely in a reactor filled with $\alpha,\alpha,\alpha',\alpha'$-tetrachloro-p-xylene in the presence of the catalysts, and then to complete the reaction if desired, in a vapor-phase reactor. It is also possible, however, to use the first reactor without catalyst, vaporize therein substantially naught but $\alpha,\alpha,-\alpha',\alpha'$-tetrachloro-p-xylene and mix it with steam at low degrees of reaction, and perform the reaction mainly in the vapor phase reaction, which takes place rapidly and completely, in the presence of the catalysts in the vapor phase reactor.

The reaction apparatus may consist of one or two parts; a mixing system for the starting substance and steam wherein the reaction may take place partially and liquid starting substance may also be present, or a steam reactor or both. If a U-shaped tube having legs with inside diameters of, for example, 80 and 15 mm, is used, $\alpha,\alpha,\alpha',\alpha'$-tetrachloro-p-xylene delivered from a reservoir through the thinner tube and heated to the reaction temperature, may be made to react in the presence of a catalyst with steam at a reaction temperature of 120° to 250° C., especially 155° to 190° C., in a weight ratio of 30 to 0.15 parts, especially 2 to 0.4 parts, of steam to one part of $\alpha,\alpha,\alpha',\alpha'$-tetrachloro-p-xylene. The temperature of the steam may be within the range of the above-named reaction temperatures, e.g., it may be the same as the reaction temperature or slightly higher. The distribution of the steam in the melt may be performed in a known manner, e.g., by means of glass frit of varying porosity, a glass tube with many perforations, or a mixing nozzle. The height of the liquid in the column communicating with the bubble column (the leg of the U-shaped tube by which the products leave the reactor) is generally 3 to 30 cm. above the zero level. The steam and the $\alpha,\alpha,\alpha',\alpha'$-tetrachloro-p-xylene may be fed in the above-described weight ratio into the reaction chamber so fast that the speed of flow of the descending vapor mixture (with reference to the empty tube at operating temperature and pressure) will amount to approximately 5 to 50 cm/sec, especially about 10 to 30 cm/sec, at a weight ratio of steam to $\alpha,\alpha,\alpha',\alpha'$-tetrachloro-p-xylene of 0.5 to 2:1. At a steam-to-starting substance ratio of about 0.8 to 1.2:1 by weight, the velocities of flow amount to 15 to 20 cm/sec.

The steam mixture thus treated may additionally pass, in the second part of the hydrolysis apparatus or in a second reactor, through a catalysis zone having a length-to-diameter ratio of, for example, 5 to 12:1, wherein by means of an advantageously supported catalyst, the $\alpha,\alpha,\alpha',\alpha'$-tetrachloro-p-xylene and p-dichloromethylbenzaldehyde formed by partial hydrolysis, carried in the steam, may be reacted almost entirely at 200° to 400° C., using additional steam if desired.

It is advantageous to circulate the melt through the reaction zone. To the extent that a catalyst is being used, it is dissolved or suspended in the melt. The heating of the reactor can be done by heating elements provided for on the inside or preferably from the outside, but in the continuous reaction an appreciable part of the heat is desirably supplied by way of the previously heated steam.

Also the steam reactor can be of any desired shape. The starting material and the steam can be introduced separately, but the introduction of a mixture is preferred in the given quantity ratio. Also the reactor can be heated either from the outside or inside. Standing or horizontal tube reactors are preferred. In general, the catalyst in solid form can be present on a reactor bottom perforated to permit introduction of steam.

A special form of the reaction vessel for the steam reaction as well as for the reaction in the melt is a U-tube with any desired diameter and height of the legs. Preferably, one leg is of reduced diameter, through which there is fed the heated starting material. The reaction products then leave the other leg. Said other leg is named bubble column (in German: Blasensaeule). In this leg, the melt is higher, due to the fact that the column of the melt is increased through the steam contained therein and the specific weight is reduced.

Suitable catalysts are iron, iron compounds such as iron salts or iron oxides, independently of the valency of the iron, especially $FeCl_3$, and zinc salts, especially zinc chloride or zinc phosphate, in a concentration ranging from 0.1 to 10, especially from 0.4 to 2% by weight of the amount of $\alpha,\alpha,\alpha',\alpha'$-tetrachloro-p-xylene required to fill the sump, and as a 5 to 10 wt-% coating on a support, especially active carbon, and also unsupported catalysts, preferably in granulated form, in a quantity permitting the gas mixture passing through the catalyst to remain in contact with it for 0.1 to 10 seconds, especially about 0.5 to 2 seconds.

The terephthalic aldehyde, which can be intercepted in a solvent may be washed free of acid with water or aqueous alkaline agents such as solutions of NaOH $Na_2CO_3$ or $NaHCO_3$, in a counterflow washing process, for example, and then freed of solvent in vacuo, or crystallized at room temperature by concentration. The terephthalic aldehyde isolated by crystallization can be at least 98% pure and can be used directly for further reactions. Determination of the aldehyde content is performed by titration as oxime. As purities above 98%, the percentage of the partially hydrolyzed product is determined by additional gas-chromatographic analysis or by determining the chlorine content. Yields can be 80–95%.

Suitable solvents are those which dissolve the terephthalic dialdehyde and are inert with respect thereto. Particularly, chlorinated hydrocarbons are used such as 1,2-dichloroethane, methylene chloride, chloroform and carbon tetrachloride etc.

Terephthalic aldehyde serves for the preparation of polymers having semiconductor or ion conductor properties, and polymers which are used as temperature-resistant substances; also, for the preparation of stabilizers, sensitizers, dyestuffs and optical brighteners.

Since hydrolysis to dialdehydes is considered to be a slow process, even in the presence of catalysts, it is surprising that the reaction time of the present process is so short, especially in the post-reaction in the vapor phase.

It is especially advantageous that the entire reaction as well as the purification and recovery of the dialdehyde can be performed continuously. At the same time, unexpectedly high yields and purity are achieved. In the case of small-size reactors either the apparatus cost is less, or higher throughputs are achieved.

EXAMPLE 1
(without catalyst)

Apparatus is used in which the inside diameters of the legs of the U-shaped tube in the first reactor are 10 and 25 mm. The distribution of the steam into the melted $\alpha,\alpha,\alpha',\alpha'$-tetrachloro-p-xylene is performed by means of a nozzle and agitating the pump by pumping a part of the reaction mixture out of the reactor and returning it to the reactor in the form of a high-pressure jet, while the steam is injected into the reactor concentrically with the jet. With a liquid level in the column, which communicates with the bubble column about 3 cm higher than the zero level, 99.3 wt-% pure $\alpha,\alpha,\alpha',\alpha'$-tetrachloro-p-xylene and steam, in a weight ratio of 1:0.7, are injected into the melt of $\alpha,\alpha,\alpha'\alpha'$-tetrachloro-p-xylene heated to 187° ± 3° C., the amount of $\alpha,\alpha,\alpha'\alpha'$-tetrachloro-p-xylene being put through per hour amounting to 183 g. The vapor phase leaving the reactor is cooled and intercepted by the addition of 1,2-dichloroethane. After the separation of the aqueous phase from the organic phase, the latter is treated with an aqueous solution of $NaHCO_3$ to remove acid components, then washed with water and freed of solvent by vacuum distillation. After a reaction time of 30 minutes, a 4.4% aldehyde is thus obtained, and after a reaction time of three hours a terephthalic aldehyde is obtained with a maximum purity of 41% in an average total yield of 42%.

A substantial increase of the yield can be achieved by then performing the vapor phase reaction in accordance with Example 4b.

EXAMPLE 2

The same apparatus is used as in Example 1. In the presence of zinc phosphate in a quantity amounting to 1.1% of the weight of the $\alpha,\alpha,\alpha',\alpha'$-tetrachloro-p-xylene filling the sump, $\alpha,\alpha,\alpha'\alpha'$-tetrachloro-p-xylene and steam are proportioned in an average weight ratio of 1:0.44 into a melt of $\alpha,\alpha,\alpha'\alpha'$-tetrachloro-p-xylene having a purity of 99.3% by weight which is heated to 187° ± 2° C. and recirculated, the steam being distributed into the melt by means of a nozzle, and the proportioning being so controlled as to sustain an average liquid level in the column, which communicates with the bubble column of 17 cm, higher than the zero level the average quantity of $\alpha,\alpha,\alpha'\alpha'$-tetrachloro-p-xylene being put through per hour amounting to 338 g. The vapor phase leaving the reactor is intercepted as described in Example 1 and tested for reaction products. After a reaction time of 20 minutes a 60.6% pure aldehyde is obtained, and after a total of 50 minutes an 86.7% pure aldehyde is obtained from the organic phase which has been treated with an aqueous solution of $NaHCO_3$ after removal of the solvent, the average total yield being 80%.

EXAMPLE 3

The apparatus described above is used. The distribution of the steam into the melt is performed by means of a glass tube having a plurality of perforations. In the presence of zinc phosphate in a quantity amounting to 1.3% of the weight of the $\alpha,\alpha,\alpha',\alpha'$-tetrachloro-p-xylene filling the sump, $\alpha,\alpha,\alpha'\alpha'$-tetrachloro-p-xylene and steam are proportioned in an average weight ratio of 1:1 into a melt, heated to 190° C., of $\alpha,\alpha,\alpha'\alpha'$-tetrachloro-p-xylene hydrolyzed to terephthalic aldehyde to equilibrium at this temperature, the rate of delivery being such as to maintain a liquid level of 3 cm in the column, which communicates with the bubble column above the zero level, the amount of $\alpha,\alpha,\alpha'\alpha'$-tetrachloro-p-xylene put through per hour averaging 124 g. By cooling the vapor phase with 1,2-dichloroethane, a terephthalic aldehyde with a maximum purity of 94% is isolated from the organic solution in an average yield of about 84% after the acid components are removed with an aqueous solution of $NaHCO_3$, and after the solvent is removed by distillation.

EXAMPLE 4

(a) An apparatus having inside diameters of 80 and 15 mm in the legs of the U-shaped tube is used in which the distribution of the steam into the melt is performed by means of a tube with a plurality of perforations.

In the presence of zinc phosphate in a quantity of 1.9 wt-% of the α,α,α',α'-tetrachloro-p-xylene in the sump, steam and α,α,α'α'-tetrachloro-p-xylene of a purity of 99.3 wt-% are delivered in a weight ratio of 1:1.2 into a melt, heated to 182° ± 2° C., of α,α,α'α'-tetrachloro-p-xylene which has been hydrolyzed to terephthalic aldehyde to the point of equilibrium, such delivery being performed at such a rate that the height of the liquid in the column which communicates with the bubble column above the zero level is 6 cm, the amount of α,α,α'λ,α'-tetrachloro-p-xylene put through per hour averaging 1000 g.

(b) The vapor phase leaving the reactor is passed at 295° ± 5° C. through 1492 g of an active carbon catalyst coated with 5 wt-% zinc phosphate and then intercepted by extraction with 1,2-dichloroethane. After removing acid impurities by means of an aqueous solution of NaHCO$_3$ and removing the solvent a 97% terephthalic aldehyde is isolated in a yield of about 89%.

(c) A 7.6 wt-% solution of crude terephthalic aldehyde in 1,2-dichloroethane thus obtained is washed substantially free of acid with water and an aqueous solution of NaHCO$_3$, and is concentrated to a ratio of terephthalic aldehyde to 1,2-dichloroethane of 1:1.88, by weight. Crystallization at room temperature produces a 62% yield (based on pure terephthalic aldehyde) of a 99% aldehyde from an initially 93.7% product. Concentration of the mother liquor and further crystallization raises the terephthalic aldehyde yield to 77.2%.

EXAMPLE 5

The apparatus described in Examples 1 to 3 is used; the distribution of the steam is accomplished by means of a nozzle and sump recirculation. In the presence of zinc phosphate in a quantity amounting to 0.7% of the weight of the α,α,α'α'-tetrachloro-p-xylene contained in the sump, steam and α,α,α'α'-tetrachloro-p-xylene of a purity of 99.3% by weight are proportioned, in a weight ratio of 1:1.6, into a melt, heated to 152° ± 3° C., of α,α,α'α'-tetrachloro-p-xylene which has been hydrolyzed to terephthalic aldehyde to equilibrium at this temperature, the proportioning being such as to maintain the level in the column communicating with the bubble column 7.5 cm above the zero level, the amount of α,α,α',α'-tetrachloro-p-xylene being put through per hour being 70 grams. The vapor phase leaving the reactor is passed at about 290° C. through 67 g of an active carbon catalyst coated with 5 wt-% zinc phosphate, and is then extracted with 1,2-dichloroethane. After the removal of acid impurities by means of an aqueous solution of NaHCO$_3$ and the removal of the solvent, a 95.3% pure terephthalic aldehyde is isolated in a yield of 87%.

EXAMPLE 6

A U-shaped reactor having inside diameters of 31 and 9 mm in the legs is used, the distribution of the steam into the melt being performed by means of a glass frit. In the presence of FeCl$_3$ in an amount equal to 0.4% of the weight of the α,α,α',α'-tetrachloro-p-xylene in the sump, steam and α,α,α',α'-tetrachloro-p-xylene in a purity of 97.2% by weight are delivered in an average ratio of 1:0.6 by weight into a melt of α,α,α',α'-tetrachloro-p-xylene heated to approximately 190° C., such delivery being performed at a rate which maintains the level in the column communicating with the bubble column 9 cm above the zero level, an average throughput of 208 g of α,α,α'α'-tetrachloro-p-xylene per hour being achieved. The vapor mixture is passed at 220° C. through 117 g of an active carbon catalyst coated with 10 wt-% FeCl$_3$, whose temperature rises to 360° C. in the course of the hydrolysis, and then it is treated in an extraction column with 1,2-dichloroethane. After the removal of acid components with an aqueous solution of NaHCO$_3$, and the extraction of the solvent, a 97.4% pure terephthalic aldehyde is obtained in an 85% yield.

What is claimed is:

1. Process for the production of terephthalic dialdehyde by hydrolysis of α,α,α',α'-tetrachloro-p-xylene, which consists essentially of contacting liquid α,α,α',α'-tetrachloro-p-xylene and steam in a weight ratio of steam to α,α,α',α'-tetrachloro-p-xylene of 30–0.15 parts steam to 1 part of α,α,α',α'-tetrachloro-p-xylene at a temperature of 120°–250° C. in a vaporization zone for production of a vapor phase containing steam and α,αλ,α',α'-tetrachloro-p-xylene and contacting said vapor in a succeeding catalysis zone with an iron salt, iron oxide or a zinc salt as catalyst for the hydrolysis, at a temperature of 200°–400° C., for hydrolysis to form the terephthalic dialdehyde.

2. Process according to claim 1, wherein the dialdehyde produced is in the vapor phase and is recovered from said vapor phase by cooling for condensation thereof in solid form.

3. Process according to claim 1, wherein the dialdehyde produced is in the vapor phase is recovered from said vapor by extraction with an inert solvent for the terephthalic dialdehyde which is a chlorinated hydrocarbon.

4. Process according to claim 1, wherein said catalyst is FeCl$_3$, zinc chloride, or zinc phosphate.

5. Process according to claim 4, said catalyst being zinc phosphate.

6. Process according to claim 1, said catalyst being supported on active carbon.

7. Process according to claim 3, wherein said solvent is a chlorinated hydrocarbon having 1 to 6 carbon atoms.

8. Process according to claim 7, said solvent being 1,2-dichlorethane.

9. Process according to claim 3, wherein the solvent containing the dialdehyde is washed with an aqueous NaOH, Na$_2$CO$_3$, or NaHCO$_3$ for removal of acid impurities.

10. Process according to claim 9, said agent being an aqueous solution of sodium bicarbonate.

11. Process according to claim 1, wherein said liquid α,α,α',α'-tetrachloro-p-xylene is a melt.

12. Process according to claim 11, wherein the melt is continuously recycled with a pump.

13. Process according to claim 4, wherein said liquid α,α,α',α'-tetrachloro-p-xylene is a melt.

14. Process according to claim 13, wherein the melt is coninuously recycled with a pump.

15. Process of claim 1, wherein said contacting in the vaporization zone is carried out in the presence of a catalyst for the hydrolysis and the hydrolysis occurs partially in the vaporization zone and partially in said succeeding catalysis zone.

16. Process according to claim 15, wherein said liquid α,α,α',α'-tetrachloro-p-xylene is a melt, and the catalyst employed in each zone is zinc phosphate.

* * * * *

UNITED STATES PATENT AND TRADEMARK OFFICE
CERTIFICATE OF CORRECTION

PATENT NO. : 4,125,561
DATED : November 14, 1978
INVENTOR(S) : Klaus Redecker and Hermann Richtzenhain It is certified that error appears in the above-identified patent and that said Letters Patent are hereby corrected as shown below:

Col. 5, line 12, after " $\alpha'$ " delete  $--\lambda--$;

Col. 6, line 20, after " $\alpha$ " delete  $--\lambda--$.

Signed and Sealed this

First Day of May 1979

[SEAL]

Attest:

RUTH C. MASON
*Attesting Officer*

DONALD W. BANNER
*Commissioner of Patents and Trademarks*